United States Patent [19]
Rolando et al.

[11] Patent Number: 5,209,984
[45] Date of Patent: May 11, 1993

[54] FILMS OF RADIATION RESISTANT HEAT SEALABLE POLYMER BLENDS HAVING A SURFACE ADHESION LAYER GRAFTED THERETO

[75] Inventors: Richard J. Rolando, Oakdale, Minn.; Dennis L. Krueger, Hudson, Wis.

[73] Assignee: Minnesota Mining and Manufacturing Company, St. Paul, Minn.

[21] Appl. No.: 905,271

[22] Filed: Jun. 26, 1992

Related U.S. Application Data

[62] Division of Ser. No. 371,713, Jun. 26, 1989, Pat. No. 5,140,073.

[51] Int. Cl.$^5$ .................... B32B 25/04; B32B 25/08; B32B 27/32; C08L 23/26
[52] U.S. Cl. .................... 428/516; 428/523; 525/193; 525/240
[58] Field of Search .............. 428/516, 523; 525/240, 525/193

[56] References Cited

U.S. PATENT DOCUMENTS

| | | | |
|---|---|---|---|
| 3,265,769 | 8/1966 | Schaffhausen | 260/889 |
| 3,299,176 | 1/1967 | Longworth | 260/876 |
| 3,372,049 | 3/1968 | Shaffhausen | 525/240 |
| 3,449,154 | 6/1969 | Katz | 117/93.1 |
| 3,634,218 | 1/1972 | Gotohda et al. | 204/159.17 |
| 3,635,631 | 1/1972 | Fields | 425/223 |
| 3,755,527 | 8/1973 | Keller et al. | 264/210 F |
| 3,836,607 | 9/1974 | Finkman et al. | 525/240 |
| 3,849,520 | 11/1974 | Bullard | 525/240 |
| 3,870,567 | 3/1975 | Palmer et al. | 136/148 |
| 3,886,056 | 5/1975 | Kitamaru et al. | 204/159.2 |
| 3,940,325 | 2/1976 | Hirao | 204/159.20 |
| 3,959,421 | 5/1976 | Weber et al. | 264/6 |

(List continued on next page.)

FOREIGN PATENT DOCUMENTS

| | | |
|---|---|---|
| 32615 | 1/1968 | Australia . |
| 633823 | 1/1962 | Canada . |
| 0068555 | 6/1982 | European Pat. Off. . |
| 0087294 | 2/1983 | European Pat. Off. . |
| 0154071 | 6/1984 | European Pat. Off. . |
| 0248545 | 5/1987 | European Pat. Off. . |
| 0297741 | 6/1988 | European Pat. Off. . |
| 54-43274 | 4/1979 | Japan . |
| 2058802 | 9/1980 | United Kingdom . |
| 2104562 | 7/1981 | United Kingdom . |

OTHER PUBLICATIONS

Bradley, Journal of Industrial Irradiation Technology 2 (2) 93–138 (1984).
Krause, Chapter 2, Polymer Blends, Paul & Newman, Editors, Academic Press, New York (1978) pp. 16–20.
Mathews, Polymer Mixing Technology, Chapter 3 (Applied Science Publishers, Essex, England) (1982).
Miller, "On the Existence of Near Range Order in Isotactic Polypropylenes", Polymer One 135–143 (1960).
Publication "Processing Shell Polybutylene Film Grade Resins", Technical Bulletin SC: 391-79 (Shell Chemical Co.) 1979.
Wente, Van A. et al., Manufacture of Superfine Organic Fibers, Report #4364 of the Naval Research Laboratories, May 25, 1984.
Wente, Van A., "Superfine Thermoplastic Fibers, Industrial Engineering Chemistry", vol. 48, No. 8, 1956 pp. 134–1346.
Kostoski et al., "Mechanical & Thermal Properties of Gamma-Irradiated iPP-LDPE Blends", Radiation Physical Chemistry vol. 28, #3 pp. 269–272.
Natta et al., Structure & Properties of Isotactic Polypropylene, Del Nuovo Cimento, Supplements A1, vol. XIV, Series X, n. 1, 1960, pp. 40–51.
Spadaro et al., "Tensile Properties of Gamma-Irradiated LDPE-iPP Blends", Radiation Physical Chemistry, vol. 23, No. 4, pp. 445–448 (1984).
Williams, "Radiation Stability of Polypropylene", ANTEC-87, pp. 1198–1200.

(List continued on next page.)

Primary Examiner—Carman J. Seccuro, Jr.
Attorney, Agent, or Firm—Gary L. Griswold; Walter N. Kirn; John H. Hornickel

[57] ABSTRACT

Polymer blends of non-crystalline mesomorphous polypropylene and a polymer compatible with such polypropylene and the method of making such polymer blends are provided. Such compatible polymer blends exhibit substantial maintenance of structural integrity after exposure to gamma irradiation and provide heat sealing properties, puncture resistance, and tear strength. Films, fibers, and other articles made from such blends may be used in various applications, including medical articles such as medical packaging films, ostomy pouches, and transdermal delivery patches, which may require sterilized storage prior to usage.

2 Claims, 4 Drawing Sheets

U.S. PATENT DOCUMENTS

| | | | |
|---|---|---|---|
| 3,987,001 | 10/1976 | Wedel et al. | 260/32.8 R |
| 4,075,290 | 2/1978 | Denzel et al. | 525/240 |
| 4,110,185 | 8/1978 | Williams et al. | 204/159.2 |
| 4,113,595 | 9/1978 | Hagiwara et al. | 204/159.17 |
| 4,274,932 | 6/1981 | Williams et al. | 204/159.2 |
| 4,300,988 | 11/1981 | Berejka et al. | 204/159.2 |
| 4,407,846 | 10/1983 | Machi et al. | 427/35 |
| 4,431,497 | 2/1984 | Rekers | 204/159.2 |
| 4,460,445 | 7/1984 | Rekers | 204/159.2 |
| 4,467,065 | 8/1984 | Williams et al. | 524/296 |
| 4,478,772 | 10/1984 | Takagi et al. | 264/22 |
| 4,563,388 | 1/1986 | Bonk et al. | 428/304.4 |
| 4,569,736 | 2/1986 | Kosegaki et al. | 523/105 |
| 4,594,203 | 6/1986 | Hagiwara et al. | 264/22 |
| 4,595,726 | 6/1986 | Klosiewicz | 525/71 |
| 4,645,792 | 2/1987 | Chatterjee | 525/240 |
| 4,710,524 | 12/1987 | Donohue | 522/75 |
| 4,739,025 | 4/1988 | Burch | 526/348.1 |
| 4,797,438 | 1/1989 | Kletecka et al. | 524/100 |
| 4,931,230 | 6/1990 | Krueger et al. | |
| 4,950,549 | 8/1990 | Rolando et al. | |

OTHER PUBLICATIONS

Nishimoto et al., "Material Design of Radiation Resistant Polypropylene: Part II-Importance of the Smectic Structure Produced by Quenching Treatment", Polymer Degradation & Stability, vol. 14 (1986) pp. 199-208.

Rolando et al., "The Influence of Morphology on the Tensile Properties of Polypropylene", ACS Polymer Material Science & Engineering, 1985 vol. 52 pp. 76-79.

Tozzi et al., "Recent Progress in the Stabilization of Polypropylene Fibers", Textile Research Journal, Aug. 1978, pp. 433-436.

Pinner, S. H., Editor, Weathering & Degradation of Plastics, Gordon & Breech Science Publishers Inc., New York, 1966, pp. 104-118.

Geil, Polymer Single Crystals, Interscience, N.Y., 1963, p. 270.

Hsiue, et al., Preirradiation Grafting of Acrylic & Methacrylic Acid onto Polyethylene Films: Preparation & Properties, J. of Applied Polymer Science vol. 30, 1985, pp. 1023-1033.

Shkolnik et al., Radiation-Induced Grafting of Sulfonates on Polyethylene, J. of Applied Polymer Science, vol. 27, 1982, pp. 1289-2196.

Chemical Abstracts, vol. 77, 1972, p. 75, Abstract No. 153607t.

Skoroszewski, "Parameters Affecting . . . Polymer Blends", Plastics and Polymers, vol. 40-No. 147, pp. 142-151.

Kawase, Kaoru et al., "Thermal Properties of Methyl Methacrylate-Grafted Polypropylene Fibers", Nippon Kagaku Kaishi, 1972 (8) pp. 1432-1437.

Higdon, Mechanics of Materials, (John Wiley, New York), 1976 pp. 104-106.

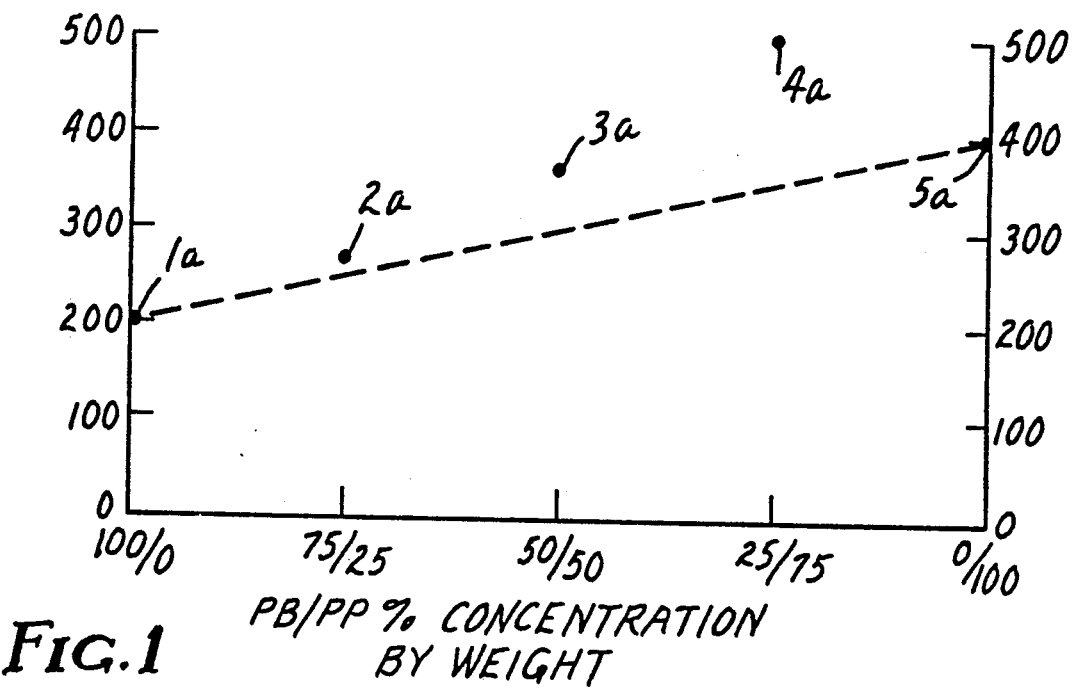
FIG.1  PB/PP % CONCENTRATION BY WEIGHT
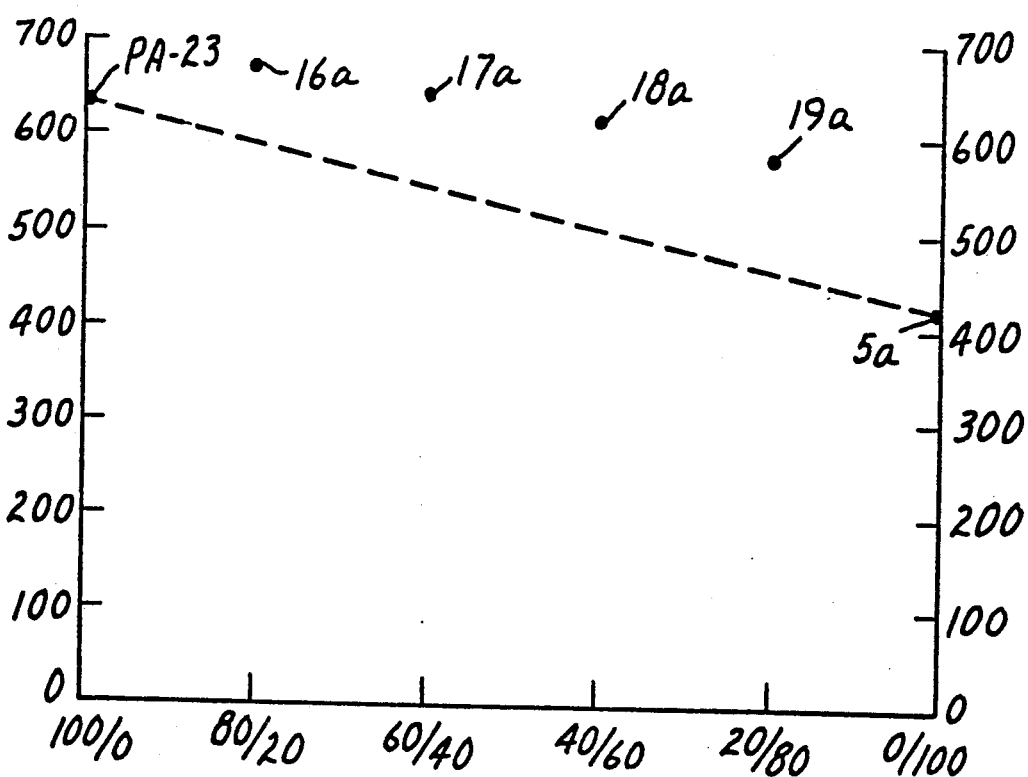
FIG.7  EXXELOR PA-23/PP % CONCENTRATION BY WEIGHT

FILMS OF RADIATION RESISTANT HEAT SEALABLE POLYMER BLENDS HAVING A SURFACE ADHESION LAYER GRAFTED THERETO

This is a division of application Ser. No. 07/371,713 filed Jun. 26, 1989, now U.S. Pat. No. 5,140,073.

FIELD OF THE INVENTION

This invention relates to polymer blends of compatible polymers resistant to the effects of sterilization irradiation, methods for preparing such polymer blends, and articles, such as fibers, films, and nonwoven fabrics incorporating such polymer blends. More particularly, this invention relates to polymer blends of non-crystalline mesomorphous polypropylene and polymers compatible with such polypropylene. Films of such blends may be used as heat sealable packaging for medical articles requiring sterilized storage, heat sealable backings for transdermal delivery medical packaging, or as heat sealable components for use as ostomy pouches also possibly requiring sterilized storage.

BACKGROUND OF THE INVENTION

Polypropylene is often a material of choice for medical articles due to its various properties such as non-toxicity, chemical resistance and inertness to drugs and liquid media used with drugs, as well as its low cost and ease of processing by means of extrusion, molding, and the like.

However, a disadvantage of crystalline polypropylene is its inherent inability to be heat sealed against another material. Medical articles or packaging for medical articles often require heat sealing in the manufacturing process to assemble the components of the article or the packaging process to protect the active ingredient or medical article in the packaging from undesired exposure.

Medical articles requiring additional protection beyond secure heat sealing in manufacturing or packaging processes can be sterilized at the time of production and thereafter maintained in a sterile condition during storage. Not all medical articles require sterilization prior to usage. But structural components resistant to radiation are more versatile for uses in medical articles and packaging than components unable to maintain structural integrity after irradiation. Thus, the most desirable material for a medical article or the packaging therefor is one which possesses resistance to the structurally demanding forms of sterilization even if current usages of the medical articles do not require such sterilization.

A preferred method of sterilization uses gamma radiation, such as radioactive cobalt 60, since it can be performed on packages sealed by heat or other methods insuring total and reliable sterility of the contents.

Unfortunately, gamma-irradiation of crystalline polypropylene causes degradation of its structural integrity (e.g., causing embrittlement, discoloration, thermal sensitivity).

To avoid such degradation, the prior art has employed a variety of stabilizers and other additives. European Patent Publication 0248545 (assigned to the same assignee as for this application), the prior art therein described the efforts undertaken to stabilize crystalline polypropylene from degradation after irradiation.

Conversely, mesomorphous, non-crystalline polypropylene, as described in European Patent Publication 0248545, provides resistance to sterilization irradiation without the necessity of any additive or stabilizer. Control over the method of preparing such mesomorphous polypropylene causes such polypropylene to substantially maintain its structural integrity after sterilization irradiation.

Unfortunately, films for packaging and the like made from polypropylene, even noncrystalline mesomorphous polypropylene, are susceptible to tearing and puncturing that disrupt maintenance of structural integrity as a manufactured product or packaging component after assembly. Usefulness of a sterilized medical article is compromised by a puncture in a polypropylene package. Also, as described above, crystalline polypropylene is not a material which can be heat sealed against another material in order to provide either a multi-component medical article or an effective radiation sterilized package.

On the other hand, polybutylene, poly(1-butene) or poly(2-butene) or both, offers many advantages to the medical packaging art that polypropylene, mesomorphous or otherwise, lacks. Polybutylene has high tear strength, high impact strength, puncture resistance. Polybutylene is also often used as a film requiring heat sealability. Reference to the versatility of polybutylene may be found in Shell Technical Bulletin sc: 391-79 (1979). However, polybutylene is highly crystalline (as much as 98% crystalline). After irradiation, the melt index of polybutylene has increased, indicating chain scission. See Bradley, *Journal of Industrial Irradiation Technology* (2) 93–138 (1984). Hence, polybutylene packaging usually degrades over the effective storage life often needed for a medical product.

Neither crystalline polyproylene nor crystalline polybutylene substantially maintain structural integrity after sterilization irradiation. Mesomorphous polypropylene lacks desirable strength packaging properties. No single polymer combines radiation resistance and several good packaging properties, e.g. tear strength, puncture resistance, and heat sealability.

Thus, what is needed is a heat sealable medical packaging material having good strength which substantially maintains its structural integrity for a useful period, even after exposure to the irradiation dosages necessary to sterilize such material.

SUMMARY OF THE INVENTION

The present invention overcomes the deficiencies of crystalline polypropylene, crystalline polybutylene and mesomorphous polypropylene for medical articles or their packaging by providing a polymer blend which has good tear strength, puncture resistance, and heat sealablity against another material and which substantially maintains its structural integrity over a useful life, even after irradiation. Such polymer blends comprise non-crystalline mesomorphous polypropylene and at least a discernible amount of a polymer "compatible" with non-crystalline mesomorphous polypropylene.

This invention concerns polymer blends of non-crystalline, mesomorphous polypropylene and a "compatible polymer".

For purposes of this invention, the definition of "polymer" includes a homopolymer, an oligomer, a mixture of a homopolymer and an oligomer, a mixture of more than one homopolymer, a mixture of more than one oligomer, a mixture of a homopolymer and a plurality of oligomers, a mixture of an oligomer and a plurality of homopolymers, or a mixture of a plurality of homopolymers and a plurality of oligomers.

The definition of "compatible" is material for an understanding of the present invention. Those skilled in the art, such as Sonja Krause in her article, "Polymer-Polymer Compatibility" appearing as Chapter 2 in *Polymer Blends*, Paul and Newman, Ed., Academic Press, New York, 1978, at pages 16–18, recognize several possible definitions of compatibility of polymers, some based on the miscibility, on a molecular scale, of homopolymers and of random copolymers. One of the definitions of polymer-polymer compatibility is that the polymer mixtures have desirable physical properties when blended.

For purposes of this invention, a blend comprising non-crystalline mesomorphous polypropylene and a "polymer compatible with said polypropylene" is a blend that at least one weight fraction has a more desirable specific physical property, a greater percent elongation at break value, than the hypothetical percent elongation at break value computed by the sum of the proportionate elongation at break values of the constituents of the blend according to the following equation:

Hypothetical percent elongation at break = ((Weight percent of mesomorphous polypropylene in the blend) × (Percent Elongation at Break of mesomorphous polypropylene)) + ((Weight percent of polymer in the blend) × (Percent Elongation at Break of the polymer)).

Expressed in other words, "compatibility" of a "polymer compatible with said polypropylene" mixed with non-crystalline mesomorphous polypropylene in a blend exists at any specific blended weight fraction when the percent elongation at break of that blend of the polymers is greater than the hypothetical value established by plotting a straight line between the percent elongations at break of the respective polymers. Graphic representations of polymer-polymer compatibility of several blends of the present invention are described in the Embodiments of the Invention.

It is desirable, but not necessary, for a blend of the present invention to have a consistently greater percent elongation at break value as compared with the hypothetical linear value of the percent elongation at break for the blends across a variety of weight fraction. But it is necessary within the scope of the present invention to have at least one blend weight fraction have a percent elongation at break value which is greater than the hypothetical linear value for that blend weight fraction.

The percent elongation at break property for polymer blends is chosen as the physical property for determination of compatibility because it is the best measurement to record the effects of irradiation of the polymer blend. A polymer blend which does not substantially maintain its structural integrity during at least two months after sterilization irradiation begins to rapidly degrade or embrittle. Percent elongation at break measures the extent of degradation or embrittlement. A substantially constant percent elongation at break measured over several months after irradiation is indicative of substantial maintenance of structural integrity of a polymer blend over that period after irradiation.

The invention further provides a method for the preparation of the polymer blend by the blending of polypropylene and a polymer compatible therewith, extruding such blend of polymers, quenching such extruded polymer blend immediately after extruding to provide a mesomorphous polymer blend having non-crystalline mesomorphous polypropylene contained therein.

The present invention describes and utilizes a blend of non-crystalline, mesomorphous polypropylene with a polymer or polymers compatible with such polypropylene. These blends optimize the combined physical properties of resistance to radiation, if needed, provided by such non-crystalline, mesomorphous polypropylene with other desirable medical packaging properties not found in polypropylene but provided by the compatible polymer, e.g. toughness, puncture resistance, and the like.

For an additional appreciation of the scope of the present invention, a more detailed description of the invention follows, with reference to the drawings.

BRIEF DESCRIPTION OF THE DRAWINGS

FIG. 1 is a graph comparing percent elongation at break values for Examples 1–5 with hypothetical linear values for Examples 1–5.

FIG. 7 is a graph comparing percent elongation at break values for Examples 16–19 with hypothetical linear values for Examples 16–19.

EMBODIMENTS OF THE INVENTION

Figure 2:
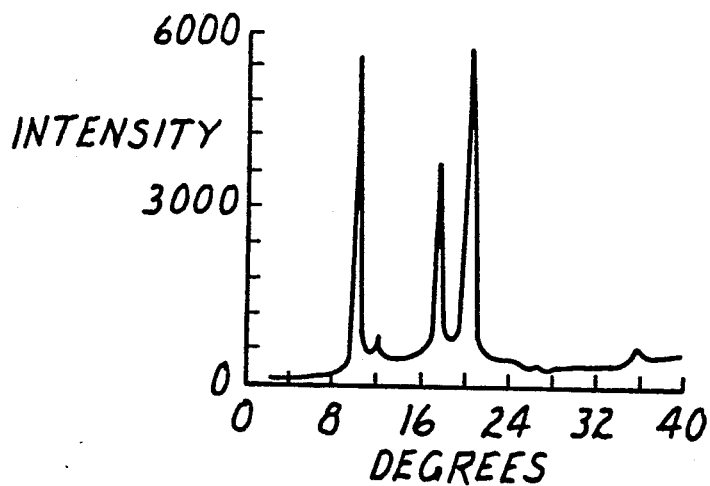
FIG. 2 is the x-ray diffraction pattern of crystalline polybutylene of Example 1.

The polymer blends of compatible polymers of the present invention substantially maintain their structural integrity for a useful period after irradiation. The blends are produced from non-crystalline mesomorphous polypropylene blended with a polymer compatible with such polypropylene.

As described above, compatibility of a polymer with non-crystalline mesomorphous polypropylene is determined by a comparison of the percent elongation at break of a weight fraction of a blend with the hypothetical value of percent elongation at break at that weight fraction as determined by the respective blended polymers in their proportionate weight fraction.

Graphically, the determination of a blend of a "compatible polymer" and non-crystalline mesomorphous polypropylene is apparent from an examination of FIG. 1, depicting the unirradiated, zero duration results from Table I below. The percent elongation at break of each example of the blend is greater than the hypothetical value of the percent elongation at break for that blend in that weight fraction. Therefore, each of the weight fractions of the blends is a mixture of non-crystalline mesomorphous polypropylene and a "polymer compatible with said polypropylene".

The number of polymers compatible with the non-crystalline mesomorphous polypropylene appear limited. It has been found that polymers compatible with non-crystalline mesomorphous polypropylene include polybutylene (melt index from about 0.4 to about 100); and certain polyolefin elastomers produced by Exxon Corporation, such as Exxelor PA-23, which is believed to be an ethylene based elastomer; This list of polymers is not necessarily exhaustive of polymers compatible with mesomorphous polypropylene as "compatible" is defined herein.

The optimum weight fraction of the compatible polymer with the mesomorphous polypropylene depends upon the ultimate intended use of the blend and the desired properties. Generally, it is desirable to add as much compatible polymer as possible to provide strength, heat sealability, and other packaging properties without compromising the radiation resistance provided by the mesomorphous polypropylene.

However, it is within the scope of this invention to add a discernibly minimal amount of the compatible polymer to mesomorphous polypropylene to provide a blend quenched to preserve mesomorphous polypropylene, having excellent sterilization irradiation resistance and better physical properties such as elongation at break than the mesomorphous polypropylene homopolymer. If the polymer blend having a minimal weight fraction of the compatible polymer can be discerned to have a greater percent elongation at break value than the hypothetical linear value computed according the equation described in the Summary of the Invention above, then the polymer blend is within the scope of this invention.

Optionally, as little as one percent by weight of the compatible polymer to the weight of the polymer blend, quenched to preserve mesomorphous polypropylene, may form an acceptable polymer blend for certain medical packaging devices to provide a radiation resistant blend having some desirable packaging properties.

It is within the scope of this invention to add a discernibly minimal amount of polypropylene to the compatible polymer to provide a blend, quenched to preserve mesomorphous polypropylene, having excellent medical packaging properties and acceptable radiation resistance. Analogously, if the polymer blend having a minimal weight fraction of mesomorphous polypropylene can be discerned to have a greater percent elongation at break value than the hypothetical linear value computed according to the equation described in the Summary of the Invention above, then the polymer blend is within the scope of this invention.

Optionally, as much as ninety-nine percent (99%) by weight of the compatible polymer to the weight of the polymer blend, may form an acceptable blend for certain medical packaging purposes.

Desirably, the weight fraction range of the compatible polymer is from about five percent (5%) to about ninety-five percent (95%) by weight of the compatible polymer to the weight of the polymer blend and more desirably from about ten percent (10%) to about ninety percent (90%) by weight of the compatible polymer to the weight of the polymer blend.

Preferably, for balance of the best properties of mesomorphous polypropylene and the compatible polymer in the blend, a weight fraction of the compatible polymer ranges from about twenty percent (20%) to about eighty percent (80%) by weight of the compatible polymer to the weight of the polymer blend, more preferably from about twenty-five (25%) to about seventy-five percent (75%) by weight of the compatible polymer to the weight of the polymer blend, and most preferably from about forty percent (40%) to about sixty percent (60%) by weight of compatible polymer to the weight of the polymer blend.

Totally optionally, to provide specific additional properties to the polymer blend, the polymer blends of the present invention may also contain conventional additives such as antistatic materials, pigments, dyes, plasticizers, ultraviolet absorbers, nucleating agents, quenching agents such as mineral oil in weight fractions to the polymer blend of about 30-40 percent, and the like. However, the blends do not require any stabilizers, anti-oxidants or the like to enable the blend to withstand the effects of irradiation and substantially maintain structural integrity for a useful period after irradiation.

The process of blending known mixtures of polymers is well known to those skilled in the art. The available methods of blending are well described in the literature, such as, Mathews, *Polymer Mixing Technology*, Chapter 3 (Applied Science Publishers, Essex, England, 1982) incorporated herein by reference. In the case of the present invention, the method of blending involves the use of an extruder by feeding the polymers (in the proper weight percentages) that had been dry-blended together prior to the heated extrusion process.

The polymer blend can be extruded from the polymer melt in any shape which can be rapidly cooled to obtain the polymer blend The shape and/or thickness of the extruded material will be dependent on the efficiency of the quenching systems utilized. Generally, films and blown microfiber webs are the preferred extruded materials.

To obtain a polymer blend having non-crystalline mesomorphous polypropylene contained therein, the extruded blend must be quenched in a manner such that primarily the mesomorphous phase of polypropylene is obtained. Miller, "On the Existence of Near-Range Order in Isotactic Polypropylenes," in *Polymer*, One 135 (1960) and in European Patent Application 87304084.4, (EPO Publication 0248545), both of which are hereby incorporated by reference herein, disclose suitable methods known to those skilled in the art for preparation of mesomorphous polypropylene.

As described by these prior publications, various known methods of quenching as soon as possible, and preferably immediately after extrusion can be used to obtain a polymer blend having non-crystalline mesomorphous polypropylene. Quenching methods include plunging the extruded material into a cold liquid, for example, an ice water bath, spraying the extruded material with a liquid such as water, and/or running the extruded material over a cooled roll or drum. Extruded polymer blended film of the present invention is preferably quenched immediately after extrusion by contact with a quench roll or by plunging the film into a quench bath. For a film thickness of from about 1.0 mil (0.025 mm) to about 10.0 mil (0.25 mm), where a quench roll is used, roll temperature is preferably maintained at a temperature below about 24° C. and the film is generally in contact with the roll until solidified. The quench roll should be positioned relatively close to the extruder die, the distance being dependent on the roll temperature, the extrusion rate, the film thickness, and the roll speed. Generally, the distance from the die to the roll is about 0.1 in. (0.25 cm) to 2 in. (5 cm). Where a quench bath is used, the bath temperature is preferably maintained at a temperature below about 40° F. (4° C.). The bath should be positioned relatively close to the die, generally about 0.1 in. (0.25 cm) to 5 in. (13 cm) from the die to the bath.

Melt blown microfibers of polymer blends of this invention are produced by extruding molten polymer through a die into a high velocity hot air stream to produce fibers having an average fiber diameter of less than about 10 microns. The fibers are generally collected on a drum in the form of a web. The preparation of microfiber webs is described in Report No. 4364 of the Naval Research Laboratories, published May 25, 1954, entitled "Manufacture of Superfine Organic Fibers," by Wente, Van A. et al. and in Wente, Van A., "Superfine Thermoplastic Fibers" in *Industrial Engineering Chemistry*, Vol. 48, No. 8, August, 1956, pp. 1342-1346, both of which are incorporated herein by reference.

To achieve webs of the polymer blends of the invention, the blown microfiber web is preferably quenched by spraying with a liquid such as water or by cooling the collector drum onto which the microfiber web is collected. Optimum quenching can be achieved by spraying the fiber web near the die, then collecting the web on a cooled drum. The water spray is preferably at a temperature of less than about 50° F. (10° C.) and less than about 1 inch (2.5 cm) from the die and the collector drum is preferably about 2 inches (5 cm) to 4 inches (10 cm) from the die, but can be as much as 8 inches (20 cm) to 10 inches (25 cm) depending on extrusion rates.

The extruded polymer blend should not be subjected to any treatment, such as orientation or stretching, at temperatures above about 60° C. because such treatment would transform the polymer blend to a structure predominantly containing crystalline polypropylene.

The polymer blends of the invention can withstand irradiation by sterilizing ionizing radiation such as gamma radiation. The dosage of gamma radiation is generally desirably in the range from about 0.1 Mrad (1.0 kGy) to about 10 Mrad (100 kGy) and preferably in the range from about 1.0 Mrad (10 kGy) to about 6.0 Mrad (60 kGy) for sterilization of medical articles.

The following non-limiting examples are provided to further illustrate the invention.

EXAMPLES 1-5

Polypropylene (Cosden 8771, melt index=9) and polybutylene (Shell 0400, melt index=20), with a variation of weight percentage by weight shown in Table I for Examples 2-4 were blended by dry blending in the respective weight percentages and then fed into the extrusion hopper of a 5.1 cm (2 Inch) Rheotec Extruder The polybutylene of Example 1 was not dry blended prior to extrusion. The extruder was operated at a flow rate of 9.08 kg/hr, having a screw speed of 20 rpm and temperature zones as follows: Zone 1: 216° C.; Zones 2-4: 244° C.; Die Zone: 244° C. to assure a melt temperature of 244° C. These Examples 1-4 were extruded into four mil (0.102 mm.) films on a chrome plated casting role in which the quench temperature was controlled at 54° F. (12.2° C.) in order for Examples 2-4 to control the non-crystalline mesomorphous structure of the polypropylene in the blend.

Example 5 was prepared by polypropylene films being extruded from Exxon PP-3014 polypropylene polymer (melt flow index - 12; average molecular weight, by GPC: 161,000) using a 1¼ inch (3.2 cm) Brabender extruder with a 12 inch (30.5 cm) wide film die at a thickness of about 1.5 mil (0.04 mm) under the following conditions:

| | |
|---|---|
| Melt temperature (°C.) | 203 |
| Screw speed (rpm) | 40 |
| Polymer flow rate (kg/hr) | 5 |
| Die temperature (°C.) | 204 |

The films were extruded onto a chrome-plated 3 inch (7.6 cm) diameter casting roll spaced 1 inch (2.5 cm) from the die. The film was in contact with the roll for about 2.5 seconds. The roll was maintained at 6.7° C.

Figure 3:
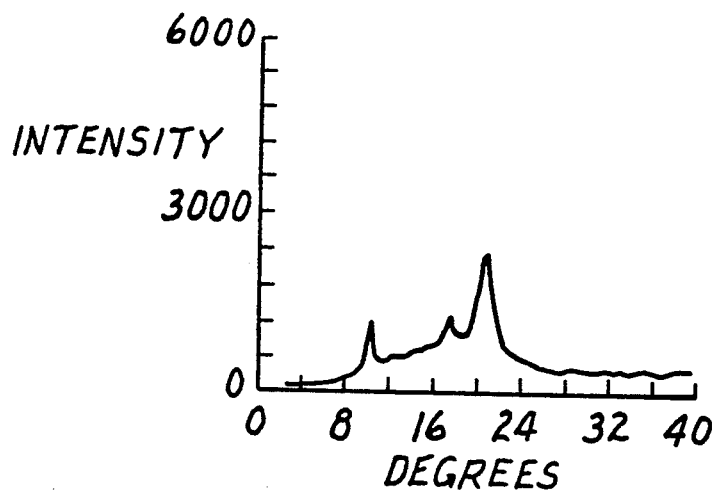
FIG. 3 is the x-ray diffraction pattern of the polymer blend of Example 2.
Figure 4:
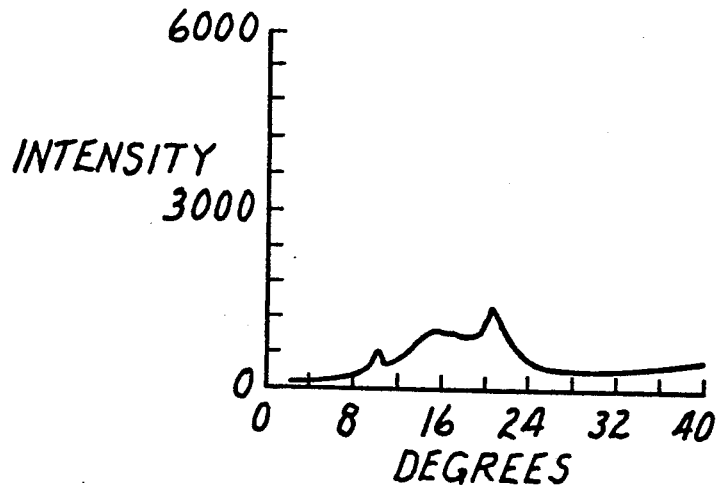
FIG. 4 is the x-ray diffraction pattern of the polymer blend of Example 3.
Figure 5:
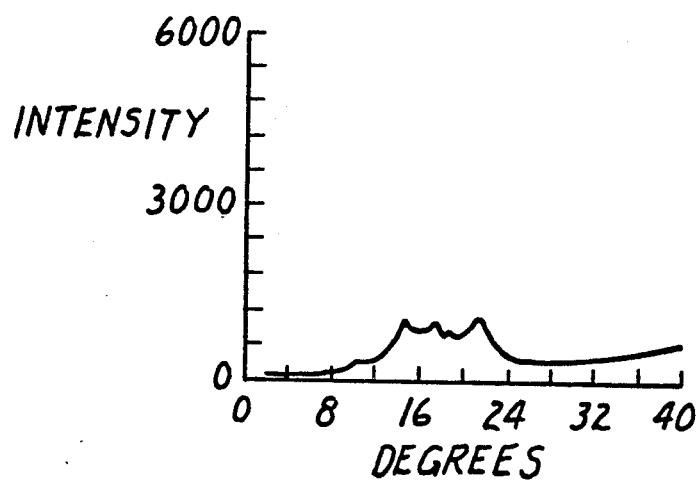
FIG. 5 is the x-ray diffraction pattern of the polymer blend of Example 4.
Figure 6:
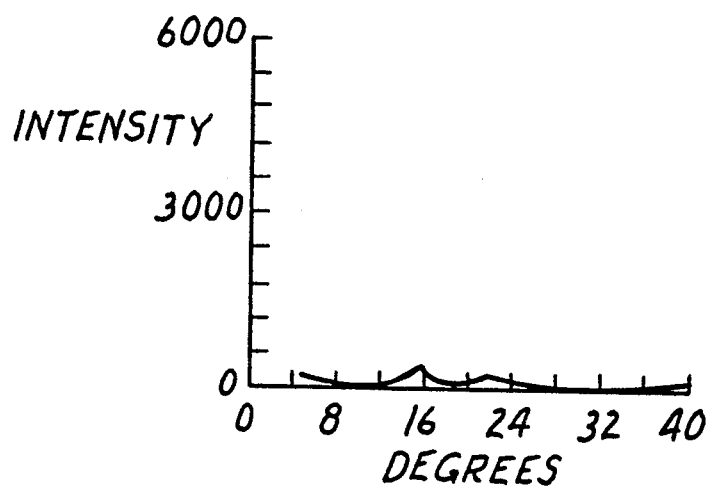
FIG. 6 is the x-ray diffraction pattern of non-crystalline mesomorphous polypropylene of Example 5.
Figure 8:
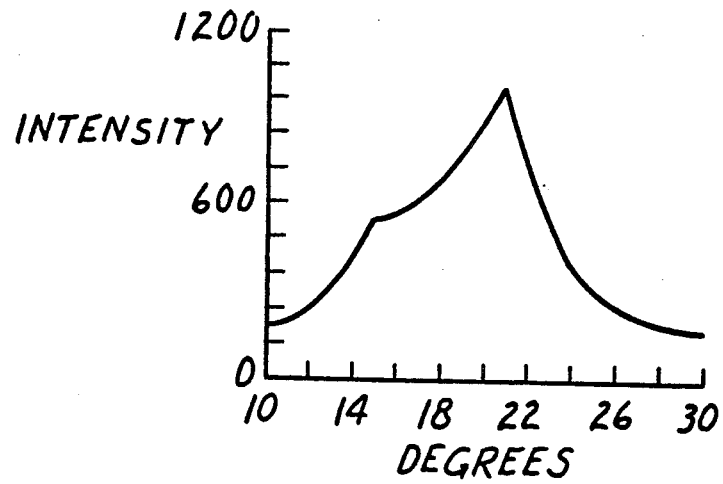
FIG. 8 is the x-ray diffraction pattern of the polymer blend of Example 16.
Figure 9:
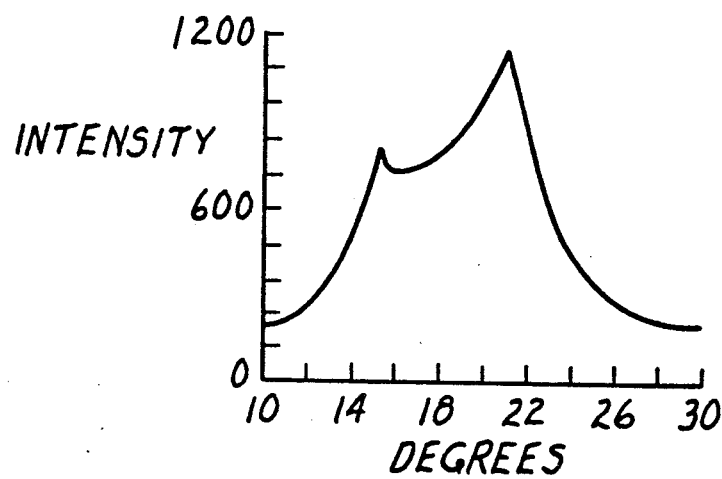
FIG. 9 is the x-ray diffraction pattern of the polymer blend of Example 17.
Figure 10:
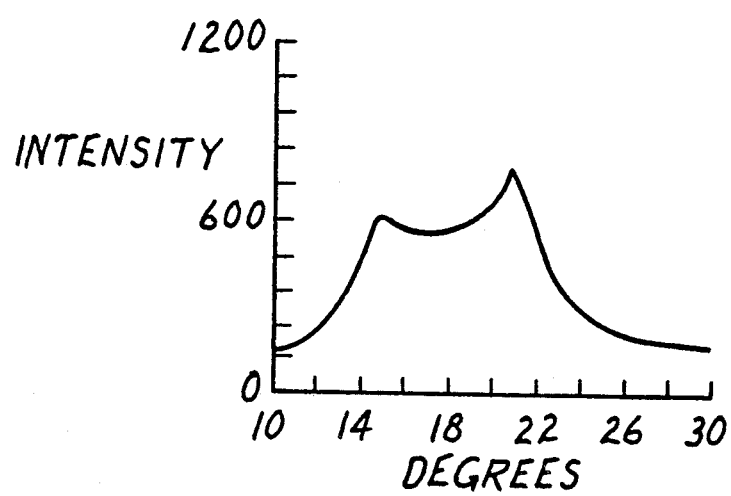
FIG. 10 is the x-ray diffraction pattern of the polymer blend of Example 18.
Figure 11:
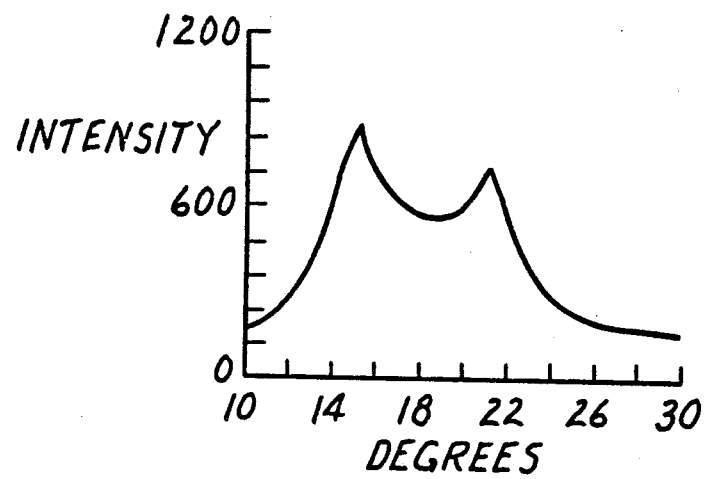
FIG. 11 is the x-ray diffraction pattern of the polymer blend of Example 19.

The crystalline structure of each Example 1-5 the blend, or absence thereof, was determined by wide-angle x-ray diffraction (WAXD). For each weight fraction Examples 1-5 there is a corresponding wide-angle x-ray diffraction graph in the FIGS. 2-6, respectively. The very sharp peaks in the WAXD graph demonstrates the high crystallinity weight fraction of pure polybutylene in FIG. 1 prepared according to Example 1. As the weight fraction of the polybutylene decreases in Examples 2-4, the less pronounced excitation peaks in the WAXD graphs of FIGS. 3-5 demonstrate the decreased relative crystallinity in the polymer blend.

Samples of each film of Examples 1b, 1c, 2b, 2c, 3b, 3c, 4b, 4c, and 5b were irradiated with gamma rays using a cobalt 60 (Co60) source in dosages indicated in Table I. Tensile properties were measured on both irradiated and unirradiated films of the various examples at various times to study the aging effects of the polymer blend and consequent degradation caused by the irradiation. Tensile measurements were performed on an Instron 1122 unit using a 2 inch × ½ inch sample size at a strain test rate of one hundred percent (100%) per minute (2 inches per minute) and using the ASTM D882-31 procedure.

Each of the Examples 1-5 was measured for percent elongation at break using ASTM D882-31 procedure, the results of which are tabulated in Table I.

TABLE I

Percent Elongation at Break of Compatible Polymer Blends With and Without Irradiation

| Example | PB/PP Weight Percent | Irradiation Dosage (kGy) | % Elongation at Break After | | | | | | |
|---|---|---|---|---|---|---|---|---|---|
| | | | 0 mths. | 2 mths. | 3 mths. | 4 mths. | 5 mths. | 6 mths. | 9 mths. |
| 1a | 100/0 | 0 | 200 | — | 200 | — | — | 200 | 200 |
| 1b | 100/0 | 30 | 200 | 200 | 200 | 180 | 150 | 150 | 125 |
| 1c | 100/0 | 60 | 200 | 150 | 130 | 75 | 45 | 25 | 0 |
| 2a | 75/25 | 0 | 270 | — | 270 | — | — | 270 | 270 |
| 2b | 75/25 | 30 | 270 | 270 | 270 | 270 | 270 | 270 | 270 |
| 2c | 75/25 | 60 | 270 | 270 | 270 | 270 | 250 | 240 | 270 |
| 3a | 50/50 | 0 | 370 | — | 350 | — | — | 410 | 390 |
| 3b | 50/50 | 30 | 370 | 370 | 370 | 370 | 390 | 380 | 340 |
| 3c | 50/50 | 60 | 370 | 360 | 400 | 360 | 360 | 370 | 410 |
| 4a | 25/75 | 0 | 500 | — | 500 | — | — | 500 | 500 |

TABLE I-continued

Percent Elongation at Break of Compatible Polymer Blends With and Without Irradiation

| Example | PB/PP Weight Percent | Irradiation Dosage (kGy) | % Elongation at Break After | | | | | | |
|---|---|---|---|---|---|---|---|---|---|
| | | | 0 mths. | 2 mths. | 3 mths. | 4 mths. | 5 mths. | 6 mths. | 9 mths. |
| 4b | 25/75 | 30 | 500 | 500 | 520 | 500 | 510 | 500 | 500 |
| 4c | 25/75 | 60 | 500 | 520 | 460 | 480 | 500 | — | 450 |
| 5a* | 0/100 | 0 | 420 | >400 | >400 | — | — | >400 | — |
| 5b* | 0/100 | 30 | >400 | >400 | >400 | — | — | >400 | — |

The polymers of polybutylene and non-crystalline mesomorphous polypropylene are compatible polymers and form an excellent blend in a broad range of mixtures according to the objects of the present invention. Polybutylene and mesomorphous polypropylene are clearly compatible polymers because the blends throughout the range of mixing exhibit a greater percent elongation at break value than hypothetical linear value at the same blend weight fraction as calculated according to the equation described in the Summary of the Invention above. As seen in FIG. 1, the actual measured percent elongation at break value exceeds the hypothetical linear value for each of Examples 2a, 3a, and 4a. Further, Example 4a has an even greater percent elongation at break value than mesomorphous polypropylene homopolymer. Thus, a blend of polybutylene as the compatible polymer is within the scope of the present invention throughout at least nearly the entire range of possible weight fractions.

When subjected to a moderate dose of gamma radiation, polybutylene of Example 1 begins to degrade within four months after irradiation. When subjected to more extreme radiation, the polybutylene of Example 1 begins degrading within two months. Hence, polybutylene alone is not a successful candidate for medical packaging requiring any significant storage time between irradiation and use.

A blend of mesomorphous polypropylene with polybutylene throughout the weight fractions shown in Examples 2-4, demonstrates substantial maintenance of structural integrity and resistance to irradiation degradation at dosages as much as 6.0 Mrad (60 kGy). Indeed, the blends of Examples 3a-c and 4a-c compare favorably in this respect with pure mesomorphous polypropylene of Example 5a-b. This result indicates the blends of this invention appreciably lose none of the radiation resistance provided by mesomorphous polypropylene while providing through careful choice(s) of compatible polymer the packaging properties mesomorphous polypropylene clearly lacks. The blends substantially maintain their structural integrity for useful storage periods, even after irradiation.

Having determined the desired available useful duration of resistance to sterilization irradiation, and then choosing various other properties such as puncture resistance, tear strength and the like desired for the blend as a medical packaging article, one can obtain an acceptable blend within the scope of the present invention.

Yield and break tensile strengths are also indicative of desirable packaging property of tear strength. Table II demonstrates the same five Examples where yield tensile strength and break tensile strength are measured at irradiation dosages of 6 Mrad (60kGy) for a period up to nine months.

TABLE II

Irradiated Compatible Polymer Blend Tensile Strength

| Example | WAXD Figure | PB/PP Weight Percent | Irradiation at 60 kGy Yield Tensile (kg/cm$^2$) | | Irradiaion at 60 kGy Yield Tensile (kg/cm$^2$) | |
|---|---|---|---|---|---|---|
| | | | t = 0 | t = 9 mths. | t = 0 | t = 9 mths. |
| 1 | 2 | 100/0 | 309.34 | * | 323.40 | * |
| 2 | 3 | 75/25 | 154.67 | 146.94 | 316.37 | 308.64 |
| 3 | 4 | 50/50 | 144.83 | 153.26 | 284.73 | 274.19 |
| 4 | 5 | 25/75 | 202.48 | 213.02 | 246.07 | 240.44 |
| 5 | 6 | 0/100 | 175.76 | 182.79 | 186.31 | 199.67 |

*Too brittle to measure.

The data of Table II indicate substantial maintenance of tensile strength for the blends of Examples 2-4 for at least nine months after irradiation and better irradiated break tensile strength of such blends over the tensile strength of mesomorphous polypropylene of Example 5 under the same irradiated conditions.

Break tensile strength of the mesomorphous polypropylene homopolymer of Example 5 is the lowest of all Examples. Conversely, break tensile strength for polybutylene homopolymer of Example 1 is the highest and occurs immediately after irradiation at 6 Mrad (60 kGy). Degradation of polybutylene homopolymer nine months later is too severe even to allow measurement of the tensile strength. Thus, break tensile strength of the blends of Examples 2-4 increases with increasing polybutylene weight fraction, and the break tensile strength of these blends is substantially maintained for at least nine months after irradiation at 6 Mrad (60 kGy). Unexpectedly, the tensile strength of mesomorphous polypropylene destined for irradiation will be improved when such polypropylene is blended with a compatible polymer that alone suffers degradation from such irradiation.

A polymer blend of mesomorphous polypropylene and polybutylene exhibits the property of resistance to sterilization irradiation exclusively found in mesomorphous polypropylene and exhibits the break tensile strength predominantly found in polybutylene, even after exposure to sterilization radiation, which would otherwise embrittle the polybutylene homopolymer. Moreover, because low molecular weight polymers, e.g., polybutylene are well known in the art as being puncture resistant, having good tear strength and being capable of being heat sealed to like materials, its presence in the polymer blend encourages the blend to be used in applications where such packaging properties are required.

EXAMPLES 6-10

Medical articles or their packaging often require manufacture or closure by heat sealing a film to itself or against another material. A polymer blend possessing resistance to structurally destructive forms of sterilization should demonstrate acceptable heat sealability.

Examples 6-10 were tested for their heat sealability, against themselves, respectively, or other similar useful heat sealable materials.

Table III below demonstrates how blends of the present invention respond to heat sealing strength tests when heat sealed to other materials including themselves. Crystalline polypropylene heat seal tear strength is provided for comparison purposes Examples 6-10 were prepared in a similar manner as those of Examples 1-5 using a 2 Inch Berlyn Extruder operated at a flow rate of 9.08 kg/hr, having a screw speed of 37 rpm and a Die Temperature of 221° C. to assure a melt temperature of 221° C. The blends were extruded into 3.5 mil (0.089 mm) films on a role chilled to 32° F. (0° C.). The crystalline polypropylene was prepared by using bi-axial orientation methods under elevated temperature conditions.

Each of the films were tested by heat sealing such samples using pressures of 40 pounds per square inch (2.8122 kg/cm$^2$) for 4 seconds to:

(1) a 3.0 mil (0.0765 mm) film made from low density polyethylene (LDPE) (available from Quantum Resin and branded as NPE 963-2PE) at 210° C.;

(2) a film of CoTran Controlled Caliper ethylene vinyl acetate (EVA), MSP98793, (available from Minnesota Mining and Manufacturing Company of St. Paul, Minn.) at 210° C.;

(3) a film of Celgard 2400 microporous polypropylene membrane available from Hoescht-Celanese Corporation at 199° C.; and (4) to another sample of the same film (self) at 199° C.

Then, each of the films were placed in an Instron 1122 machine to measure tear strength of the heat sealed portions of the samples. Constantly increasing force was applied to pull an unsealed portion of each sample at a 90° angle from the heat sealed portion. The heat seal strength data in Table III show the forces at which the heat seals began to fail.

TABLE III

| Example | PB/PP Weight Percent | Heat Seal Test Strength (grams/cm) | | | |
|---|---|---|---|---|---|
| | | LDPE | EVA | Celgard | Self |
| 6 | 100/0 | 5 | 18 | 693 | 1155 |
| 7 | 60/40 | 27 | 331 | 1129 | 1143 |
| 8 | 50/50 | 27 | 255 | 1233 | 1005 |
| 9 | 40/60 | 25 | 281 | 1362 | 1278 |
| 10 | 0/100 | 13 | 317 | 746 | 1407 |
| Crystalline Polypropylene | | 13 | 229 | 161 | 16 |

The heat seal tear strength of each of Examples 6-10 to other samples of the same respective Example (self) is significantly high to merit using polymer blends of the present invention in packaging and other uses which requires heat sealing of two pieces of the same material together Also, the blends of Examples 7-9 compare favorably with polybutylene homopolymer and mesomorphous polypropylene homopolymer, in that the heat seal tear strength of the blends is not significantly lower than the respective heat seal tear strengths of the homopolymers of Examples 6 and 10. By comparison the heat seal tear strength of crystalline polypropylene is negligible.

With respect to LDPE heat seal tear strength, none of the Examples 6-10 is significantly high to be universally useful as a heat seal candidate with LDPE. However, of the Examples, the blends of Examples 7-9 have higher heat seal tear strength than the homopolymers of Examples 6 and 10 or crystalline polypropylene and may be useful for specific packaging purposes where easier heat seal release is needed.

With respect to Celgard heat seal tear strength, the blends of Examples 7-9 are excellent, stronger than either the polybutylene or mesomorphous polypropylene homopolymer films of Examples 6 and 10 and much stronger than crystalline polypropylene. The polymer blends of the present invention are excellent candidates as films to be heat sealed to films of Celgard; a well known and versatile commercial material.

With respect to EVA, the blends of Examples 7-9 compare favorably with mesomorphous polypropylene homopolymer of Example 10 and crystalline polypropylene, which surprisingly have better heat seal tear strengths than the polybutylene homopolymer of Example 6. The blends of Examples 7-9 are useful in being heat sealed to EVA.

The heat seal tear strength of mesomorphous polypropylene homopolymer compares favorably with or exceeds the heat seal strength of polybutylene homopolymer. Whereas, crystalline polypropylene has not generally been used in the medical packaging art in heat sealable applications, mesomorphous polypropylene may be useful. However, mesomorphous polypropylene otherwise lacks other desirable packaging properties such as tear strength and puncture resistance, which may be provided by blending with compatible polymers such as polybutylene.

EXAMPLES 11-15

The polymer blends of the present invention have improved high speed puncture resistance and tear strength when compared with mesomorphous polypropylene and low density polyethylene (LDPE). The test used MTS 810 materials testing unit from MTS Systems of Eden Prairie, Minn. and employing testing procedures from ASTM number D3763. Establishing the puncture rate at 7,700 inches per minute, a probe having a diameter of 1.5 inches was impacted against an unsupported sample having a diameter of 5.0 inches (12.7 cm) for each of Examples 11-15 prepared in the same manner as Examples 1-5 and LDPE prepared according to the method indicated in footnote below Table IV.

The polymer blends of the present invention also exhibit improved tear strength over mesomorphous polypropylene homopolymer. The test used the Single Tear Test method, ASTM D-1938-67, which measures the force in grams to propagate a tear across a film at a tear rate of 250 mm/min. The film samples for Examples 11-15 were 75 mm long by 25 mm wide, having a single slit 50 mm long 12.5 mm from the longer edge of the sample. Table IV shows the tear strength results.

TABLE IV

| | Improved High Speed Puncture Resistance | | | |
|---|---|---|---|---|
| Example* | PB/PP Weight Percent | Thickness (mm) | Energy to Maximum Force (Joules) | Tear Resistance (Machine Direction g/cm of sample thickness) |
| 11 | 100/0 | 0.096 | 1.678 | 122,000 |
| 12 | 25/75 | 0.115 | 1.167 | 63,000 |
| 13 | 50/50 | 0.109 | 0.897 | 26,900 |
| 14 | 25/75 | 0.124 | 0.891 | 14,200 |
| 15 | 0/100 | 0.102 | 0.430 | 10,800 |
| Low Density Polyethylene (LDPE)** | | 0.102 | 0.553 | — |

*Examples 11-15 prepared in the same manner and correspond respectively to Examples 1-5.
**LDPE prepared from Dowlex 752 available from Dow Chemical Company of Midland, Michigan in the same manner as the samples of Example 5.

The data in Table IV demonstrate that the relatively thin films of the polymer blends in various weight fractions have significantly improved resistance to high speed punctures compared with mesomorphous polypropylene homopolymer or another packaging material such as LDPE. Although the resistance to puncturing decreases as the weight fraction of polybutylene in the polymer blends of the present invention decreases, there is significantly improved high speed puncture resistance in the blends of Examples 12-14 over the resistance found mesomorphous polypropylene homopolymer or LDPE homopolymer. The data in Table IV also demonstrates the improved tear strength of the blends of Examples 12-14 over the tear strength of mesomorphous polypropylene homopolymer of Example 15. Polybutylene homopolymer has excellent tear strength as seen in Example 11, which contributes to the tear strength of Examples 12-14, respectively.

Thus, while mesomorphous polypropylene has excellent radiation resistance and good heat sealability, it lacks the puncture resistance and tear strength that polybutylene can contribute to the polymer blend. For packaging purposes, the weight fractions of the mesomorphous polypropylene and the compatible polymer in the polymer blend may be determined by the relative balance of properties desired for the blend.

EXAMPLES 16-19

Other polymers compatible with mesomorphous polypropylene demonstrate the scope of the present invention. FIG. 7 is a graph analogous to the graph of FIG. 1, recording the actual percent elongation at break values to demonstrate the compatibility with mesomorphous polypropylene with Exxelor PA-23 available from Exxon Corporation, which is believed to be an ethylene-based elastomer. FIGS. 8-11 show the relative crystalline and non-crystalline morphologies for various polymer blends of mesomorphous polypropylene and Exxelor PA-23.

That variety of blends of mesomorphous polypropylene (FINA 8771, melt index=9) and Exxelor PA-23 having the weight percentages shown in Table v were extruded using a 2 Inch Rheotec Extruder operating at a flow rate of 9.08 kg/hr, a screw speed of 20 rpm and at a die zone temperature of 232° C. to assure a melt temperature of 232° C. The blends were extruded in four mil (0.10 mm) films on a chrome casting role in which the quenched temperature was controlled at a temperature less than about 22° C. in order to give a non-crystalline mesomorphous morphology for the polypropylene.

Table V identifies the correlation of each of the Examples 16-19 to the wide-angle x-ray defraction FIGS. 8-11.

Table V also identifies the percentage elongation at break after each of the examples was sterilized in the same manner as that for Examples 1-5 at 3, 6, and 10 Mrad (30, 60, and 100 kGy) sterilization doses, respectively. Storage time was extended for these Examples to twelve months.

The FIGS. 8-11 show decreasing relative crystallinity with increasing mesomorphous polypropylene weight fraction in the polymer blend.

Table V also provides the unirradiated, zero duration percent elongation at break data for each Example 16a, 17a, 18a, and 19a. The percent elongation at break for mesomorphous polypropylene is obtained from Example 5. A percent elongation at break value of 639% for Exxelor PA-23 was obtained by testing performed on the same size samples of 4.0 mil (0.102 mm) films according to the same testing procedures as that described for Examples 1-5. The graph in FIG. 7 shows that each Example 16a, 17a, 18a, and 19a of the blend has a greater percent elongation at break value than the hypothetical linear value computed according to the equation described in the Summary of the Invention above. Thus, Exxelor PA-23 is another polymer which is compatible throughout at least nearly the entire possible range of weight fractions for the polymer blend of the present invention.

TABLE V

| | | Improved Radiation Resistance for Exxelor PA-23/PP | | | | | | | | |
|---|---|---|---|---|---|---|---|---|---|---|
| | WAXD | Exxelor PA-23/PP | Irradiation Dosage | % Elongation at Break After | | | | | | |
| Ex. | Figure | Weight % | (kGy) | 0 mths. | 1 mth. | 2 mths. | 3 mths. | 6 mths. | 9 mths. | 12 mths. |
| 16a | 8 | 80/20 | 0 | 669 | — | — | — | — | — | 700 |
| 16b | 8 | 80/20 | 30 | — | 637 | 590 | 671 | 627 | 843 | 683 |
| 16c | 8 | 80/20 | 60 | — | 612 | 622 | 625 | 593 | 723 | 758 |
| 16d | 8 | 80/20 | 100 | — | 597 | 601 | 617 | 587 | 594 | — |
| 17a | 9 | 60/40 | 0 | 649 | — | — | — | — | — | 693 |
| 17b | 9 | 60/40 | 30 | — | 599 | 616 | 622 | 654 | 820 | 667 |
| 17c | 9 | 60/40 | 60 | — | 594 | 655 | 678 | 612 | 644 | 745 |

TABLE V-continued

Improved Radiation Resistance for Exxelor PA-23/PP

| Ex. | WAXD Figure | Exxelor PA-23/PP Weight % | Irradiation Dosage (kGy) | % Elongation at Break After | | | | | |
|---|---|---|---|---|---|---|---|---|---|
| | | | | 0 mths. | 1 mth. | 2 mths. | 3 mths. | 6 mths. | 9 mths. | 12 mths. |
| 17d | 9 | 60/40 | 100 | — | 580 | 628 | 610 | 644 | 708 | 715 |
| 18a | 10 | 40/60 | 0 | 622 | — | — | — | — | — | 630 |
| 18b | 10 | 40/60 | 30 | — | 620 | 571 | 644 | 610 | 611 | 613 |
| 18c | 10 | 40/60 | 60 | — | 590 | 617 | 633 | 616 | 611 | 694 |
| 18d | 10 | 40/60 | 100 | — | 601 | 589 | 615 | 581 | 598 | 605 |
| 19a | 11 | 20/80 | 0 | 580 | — | — | — | — | — | 590 |
| 19b | 11 | 20/80 | 30 | — | 560 | 535 | 587 | 672 | 635 | 605 |
| 19c | 11 | 20/80 | 60 | — | 563 | 526 | 623 | 617 | 594 | 585 |
| 19d | 11 | 20/80 | 100 | — | 559 | 464 | 616 | 588 | 541 | 618 |

The data in Table V show that even after subjected to irradiation dosages of as much as 10 Mrad (100 kGy), blends having compatible Exxelor PA-23 in weight percents from about twenty percent (20%) to about eighty percent (80%) by weight of the polymer blend show substantial maintenance of structural integrity of the blend as long as one year, even after irradiation.

Indeed, any polymer compatible in a blend with mesomorphous polypropylene having desired properties which are otherwise lacking in the mesomorphous polypropylene homopolymer may be included within the scope of the present invention. The relative weight fractions of the mesomorphous polypropylene and the polymer compatible therewith may be balanced within that determined effective range of weight fractions according to other desired physical properties provided by the compatible polymer, such as additional heat sealing capability, impact resistance, tear strength, and the like.

COMPARISON EXAMPLES 20-25

It is important for the polymer blends of the present invention to be prepared under controlled temperature conditions. At the time of extrusion, the polymer blends must be quenched at temperatures less than from about 100° F. (38° C.). Otherwise, radiation resistance is lost. Table VI demonstrates the deleterious effect of extruding at a slow cooling temperature at about 130° F. (55° C.).

Examples 20-22 were prepared according to the same process as described for Examples 1-4 except that the cooling temperature was 130° F. (55° C.). Examples 23-25 were prepared according to the same process as for Examples 16-19 except that the cooling temperature at extrusion was 135° F. (57.2° C.). Examination of the crystallinity of the blends of each of the examples below in Table VI was made by wide angle x-ray diffraction.

TABLE VI

| Ex. | Blend | Weight % | PP Crystal Type | Irradiation Dosage (kGy) | % Elongation at Break After | | | | |
|---|---|---|---|---|---|---|---|---|---|
| | | | | | 0 mths. | 2 mths. | 4 mths. | 6 mths. | 9 mths. | 12 mths. |
| 20a | PB/PP | 75/25 | * | 0 | 280 | — | — | 310 | 270 | — |
| 20b | PB/PP | 75/25 | * | 30 | 280 | 280 | 250 | 240 | 200 | — |
| 20c | PB/PP | 75/25 | * | 60 | 280 | 200 | 120 | 40 | 10 | — |
| 21a | PB/PP | 50/50 | Crystalline | 0 | 400 | — | — | 410 | 380 | — |
| 21b | PB/PP | 50/50 | Crystalline | 30 | 400 | 400 | 370 | 310 | 270 | — |
| 21c | PB/PP | 50/50 | Crystalline | 60 | 400 | 300 | 270 | 220 | 100 | — |
| 22a | PB/PP | 25/75 | Crystalline | 0 | 500 | — | — | 480 | 500 | — |
| 22b | PB/PP | 25/75 | Crystalline | 30 | 500 | 500 | 500 | 450 | 420 | — |
| 22c | PB/PP | 25/75 | Crystalline | 60 | 500 | — | — | 400 | 150 | — |
| 23a | PA-23/PP | 80/20 | Crystalline | 0 | 681 | — | — | — | — | 662 |
| 23b | PA-23/PP | 80/20 | Crystalline | 30 | — | 440 | — | 100 | 55 | — |
| 23c | PA-23/PP | 80/20 | Crystalline | 60 | — | 410 | — | 71 | 21 | 10 |
| 23d | PA-23/PP | 80/20 | Crystalline | 100 | — | 225 | — | 37 | 12 | 5 |
| 24a | PA-23/PP | 40/60 | Crystalline | 0 | 628 | — | — | — | — | 632 |
| 24b | PA-23/PP | 40/60 | Crystalline | 30 | — | 575 | — | 250 | 150 | 40 |
| 24c | PA-23/PP | 40/60 | Crystalline | 60 | — | 540 | — | 170 | 80 | 20 |
| 24d | PA-23/PP | 40/60 | Crystalline | 100 | — | 500 | — | 80 | 15 | 7 |
| 25a | PA-23/PP | 20/80 | Crystalline | 0 | 642 | — | — | — | — | 635 |
| 25b | PA-23/PP | 20/80 | Crystalline | 30 | — | 610 | — | 410 | 200 | 65 |
| 25c | PA-23/PP | 20/80 | Crystalline | 60 | — | 580 | — | 200 | 70 | 21 |
| 25d | PA-23/PP | 20/80 | Crystalline | 100 | — | 40 | — | 13 | 11 | 11 |

*Not susceptible to determination

As may be seen from examination of Table VI, the degradation of the blends over time increases with the increase in radiation dosage. All of Examples 20-25 have lower percent elongation at break values with increased irradiation dosages, longer duration, and both. However, when comparing polymer blends of Examples 20-25 shown in Table VI with the polymer blends of the present invention of Examples 2-4 and 16-19 at comparable irradiation dosages for comparable storage times, the same weight fractions comprising the blends when quenched during extrusion at temperatures less than about 38° C., and desirably less than about 24° C. resist the structural degradation effects of sterilization irradiation.

The polymer blends of the present invention may be used for a variety of medical or other article or packaging constructions. Because the blends are radiation resistant, films or microfiber webs made from the blends and used as components in medical or other articles or packaging for medical or other articles are capable of maintaining their structural integrity over useful periods of article's shelf and use lives even if subjected to dosages of sterilizing irradiation. Because the blends are heat sealable, puncture resistant and have good tear strength, films or microfiber webs or fibrous webs made from the blends are versatile components for an article or the packaging for an article.

Some utilizations will require radiation resistance; some utilizations will require puncture resistance, tear strength, additional heat sealability, and the like; some will require both. The compatible polymer blends of the present invention can universally serve any of those utilizations even if not all of its benefits are fully being utilized.

Various possible uses of films made from blends of the present invention include packaging for medical articles, such as syringes, requiring sterilization during storage, backings for transdermal delivery patches requiring heat sealability and good tear strength and possible radiation resistance, and sidewalls for ostomy pouches requiring good tear strength, puncture resistance, and heat sealability. This listing is not and should not be construed as exhaustive of the many possible uses of the blends of the present invention.

Films of the polymer blend of the present invention may desirably have an additional layer grafted to the film to enhance other properties such as surface adhesion, permeability, coefficient of friction, or other properties desirable to those skilled in the art for the film. For example, not by way of limitation, surface adhesion is desirable in order to provide the application of primers and other coatings to a film that would not otherwise adhere well to a film of the polymer blends of the present invention.

Using the methods identified in European Patent Publication EPO 0297741, which is incorporated by reference herein, the surface adhesion layer is desirably grafted to the polymer blend by electron beam irradiation in dosages of from about 0.5 Mrad (5 kGy) to about 20 Mrad (200 kGy) and preferably about 5 Mrad (50 kGy). The compounds desirably to be grafted to the polymer blend film include acrylic acid (AA), dimethylacrylamide (DMA), N-vinyl-2-pyrrolidone (NVP), and a copolymer of NVP and trimethylolpropanetriacrylate (NVP/TMPTA). Other possible compounds to be used as a grafting layer include glycidyl acrylate, hydroxyethyl acrylate, hydroxymethyl acrylate, 2-vinyl, pyridine, sulfoethyl methacrylate, diisopropylacrylamide, or N,N-diethylamino acrylate.

Exemplary compounds were grafted onto films prepared in the same manner as that for films of Examples 2 and 4. Grafting used an electron beam generating dosages identified in Table VII in a nitrogen atmosphere at 175 kv with a web speed of 25 feet per minute (7.62 m/min).

The strength of the graft was measured using a 180° peel adhesion test described as follows: A 2.5 cm wide, 20.3 cm long strip of pressure-sensitive adhesive tape (Scotch TM brand tape no. 8411) is adhered to a 10.1 cm wide, 15.2 cm long sheet of test substrate with a free end of the tape extending beyond the end of the test substrate. The sample is rolled twice with a 1.35 kg hard rubber roller to ensure contact between the adhesive and the test substrate. The sample is aged at room temperature (22° C.) for 24 hours. The free end of the tape is removed from the test substrate at a rate of 6 inches/minute using a Slip/Peel Tester, available from Instrumentors, Inc.

Table VII displays the data for the grafted compound, its e-beam irradiation dosage, and peel adhesion results tested at various intervals over at least 6 months time.

TABLE VII

| | Peel Adhesion Results on Graft Modified Polymer Blends | | | | | |
|---|---|---|---|---|---|---|
| | Grafted | e-Beam | Peel Force (g/cm.) | | | |
| Ex. | Monomer | Irradiation (kGy) | 1 month | 3 months | 7 months | 9 months |
| 2 | Control | 50 | 138 | 124 | — | 146 |
| 2 | AA | 50 | 269 | 239 | — | 217 |
| 2 | DMA | 50 | 411 | 413 | 308 | 314 |
| 2 | NVP | 100 | 181 | 180 | 163 | 165 |
| 2 | NVP/TMPTA | 100 | 213 | 162 | 167 | 167 |
| 4 | Control | 50 | 147 | 185 | — | 161 |
| 4 | AA | 50 | 279 | 252 | — | 218 |
| 4 | DMA | 50 | 411 | 328 | 254 | — |
| 4 | NVP | 100 | 234 | 217 | 181 | 273 |
| 4 | NVP/TMPTA | 100 | 239 | 231 | 287 | — |

Throughout the range of polymer blend weight fractions, a blend having the grafted monomer of any of the compounds identified above has improved surface adhesion for at least six months after sterilization irradiation.

Table VIII compares the graft-modified polymer blends and the unmodified polymer blends in respect of elongation at break after e-beam irradiation at the dosages shown in Table VIII.

TABLE VIII

| | % Elongation at Break Comparison | | | | | |
|---|---|---|---|---|---|---|
| | Grafted | e-Beam | % Elongation at Break | | | |
| Ex. | Monomer | Irradiation (kGy) | 1 month | 3 months | 7 months | 9 months |
| 2 | Control | 50 | 315 | — | 346 | 395 |
| 2 | AA | 50 | 323 | — | 347 | 361 |
| 2 | DMA | 50 | 308 | — | 349 | 317 |
| 2 | NVP | 100 | 310 | 311 | 382 | 386 |
| 2 | NVP/TMPTA | 100 | 314 | 309 | 365 | 388 |
| 4 | Control | 50 | 525 | — | 643 | 669 |
| 4 | AA | 50 | 438 | — | 458 | 638 |
| 4 | DMA | 50 | 442 | — | 583 | 664 |
| 4 | NVP | 100 | 431 | 489 | 687 | 603 |

TABLE VIII-continued

| | Grafted | % Elongation at Break Comparison | | | | |
|---|---|---|---|---|---|---|
| | | e-Beam | % Elongation at Break | | | |
| Ex. | Monomer | Irradiation (kGy) | 1 month | 3 months | 7 months | 9 months |
| 4 | NVP/TMPTA | 100 | 423 | 561 | 598 | 624 |

The various grafted-monomer polymer blends do not suffer degradation to e-beam irradiation. Combined with the radiation resistance of the polymer blends described above, graft-modified polymer blends substantially maintain the structural integrity provided by the polymer blend of the present invention and have the benefit of the improved surface adhesion provided by the grafted-monomer layer.

While in accordance with the patent statutes, description of the preferred weight fractions, processing conditions, and product usages have been provided, the scope of the invention is not to be limited thereto or thereby. Various modifications and alterations of the present invention will be apparent to those skilled in the art without departing from the scope and spirit of the invention. The examples described in this application are illustrative of the possibilities of varying the amounts of polymer in the blend to achieve properties for specific purposes.

Consequently, for an understanding of the scope of the present invention, reference is made to the following claims.

What is claimed is:

1. A film comprising a polymer blend film and a surface adhesion grafted to said polymer blend film, the polymer blend comprising non-crystalline mesomorphous polypropylene and at least a discernable amount of polybutylene.

2. The film according to claim 1, wherein the surface adhesion layer comprises acrylic acid, dimethylacrylamide, N-vinyl-2-pyrrolidone, a copolymer of N-vinyl-2-pyrrolidone and trimethylolpropanetriacrylate, glycidyl acrylate, hydroxyethyl acrylate, hydroxymethyl acrylate, 2-vinyl pyridine, sulfoethyl methacrylate, diisopropylacrylamide, or N,N-diamino acrylate.

* * * * *